United States Patent [19]

Denzer et al.

[11] 4,113,727
[45] Sep. 12, 1978

[54] PROCESS FOR THE PREPARATION OF SUBSTITUTED ISOXAZOLO[4,5-c]PYRIDIN-4-(5H)-ONES

[75] Inventors: Max Denzer, Parsippany; Joseph A. Smith, Fanwood, both of N.J.

[73] Assignee: Sandoz, Inc., E. Hanover, N.J.

[21] Appl. No.: 790,896

[22] Filed: Apr. 26, 1977

[51] Int. Cl.$^2$ ............................................. C07D 491/04
[52] U.S. Cl. ............................... 544/362; 424/248.54; 424/250; 424/263; 260/293.59; 260/296 H; 544/127; 544/367
[58] Field of Search ................... 260/296 H; 544/127; 210/268 BC

[56] References Cited

U.S. PATENT DOCUMENTS 4,049,813  9/1977  Nadelson ..................... 260/296 H X

OTHER PUBLICATIONS

Anker et al, J. Chem. Soc. 1941, pp. 323 to 331.

*Primary Examiner*—John D. Randolph
*Attorney, Agent, or Firm*—Gerald D. Sharkin; Robert S. Honor; Timothy G. Rothwell

[57] ABSTRACT

An improved process for the preparation of substituted isoxazolo[4,5-c]pyridin-4(5H)-ones which are either useful as intermediates in the preparation of compounds having pharmaceutical activity or as hypolipidemic agents which comprises cyclizing a corresponding 5-(2-amino-2-phenyl- or substituted phenyl-ethenyl)-3-substituted-N-alkyl isoxazole-4-carboxamide under acidic conditions.

8 Claims, No Drawings

PROCESS FOR THE PREPARATION OF SUBSTITUTED ISOXAZOLO[4,5-c]PYRIDIN-4-(5H)-ONES

This invention relates to a process for the preparation of substituted isoxazolo[4,5-c]pyridin-4(5H)-ones which are useful either as intermediates in the preparation of compounds having pharmaceutical activity or as hypolipidemic agents.

The present invention, accordingly, provides an improved process for preparing compounds of the formula:

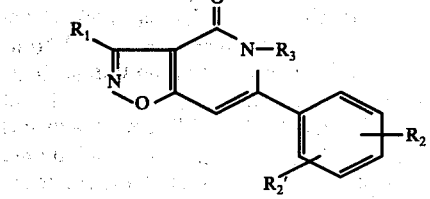
(I)

wherein $R_1$ represents lower alkyl, i.e., alkyl having 1 to 4 carbon atoms, e.g., methyl, ethyl, isopropyl and the like, cycloalkyl, i.e., cycloalkyl having 3 to 6 carbon atoms, e.g., cyclopropyl, cyclobutyl and the like, or

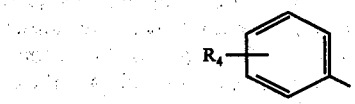

and where $R_2$, $R_2'$ and $R_4$ each independently represent hydrogen, halo having an atomic weight of about 19 to 36, i.e., fluoro or chloro, lower alkyl as defined above, lower alkoxy, i.e., alkoxy having 1 to 4 carbon atoms, e.g., methoxy, ethoxy and the like, or trifluoromethyl, and when $R_1$ represents

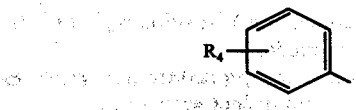

and $R_2'$ represents hydrogen, $R_2$ may also represent

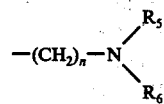

wherein $R_5$ and $R_6$ independently represent hydrogen or lower alkyl as defined above, or together with N represent

where
  X is $CH_2$, O or $N\text{-}CH_3$ and
  n is 1 to 3, and
  $R_3$ represents lower alkyl as defined above.

The compounds of formula (I) are prepared according to the following reaction scheme:

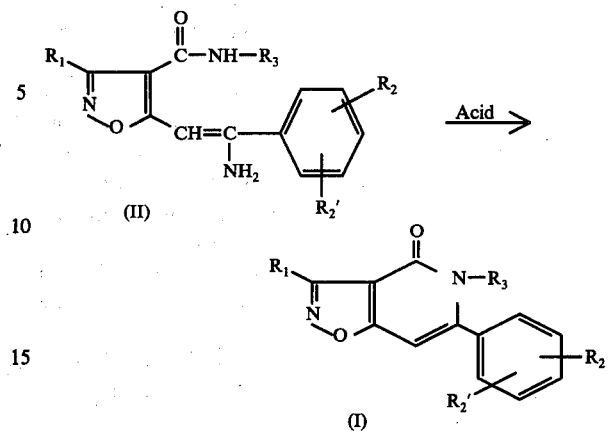

where $R_1$, $R_2$, $R_2'$ and $R_3$ are as defined above.

The compounds of formula (I) are prepared by cyclizing a compound of the formula (II) with an acid such as sulfuric acid, polyphosphoric acid, p-toluenesulfonic acid or hydrochloric acid, the latter being especially preferred, in the presence of an inert atmosphere, e.g., nitrogen, helium or argon, preferably nitrogen, and in the presence of a water miscible solvent. The particular water miscible solvent employed is not critical, but it is preferred that the reaction be carried out in the presence of acetone, dioxane, tetrahydrofuran, or the lower alkanols, e.g., methanol, ethanol and the like, preferably acetone. The temperature of the reaction is not critical but it is preferred that the reaction be carried out at a temperature of from about 15° to 100° C., preferably from about 25° to 30° C. The reaction is run from about 5 to 30 hours, preferably from about 18 to 24 hours. The product is recovered using conventional techniques, e.g., filtration.

The compounds of formula (II) are prepared according to the following reaction scheme:

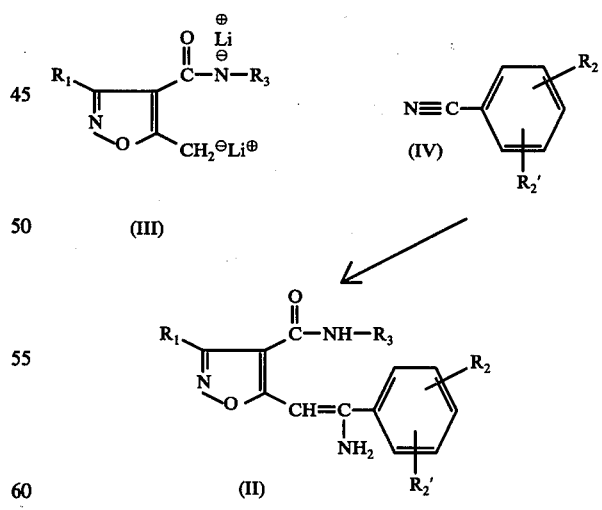

where $R_1$, $R_2$, $R_2'$ and $R_3$ are as defined above.

The compounds of formula (II) are prepared by reacting a compound of the formula (III) with a compound of the formula (IV) in the presence of an inert organic solvent. Although the particular solvent employed is not critical, it is preferred that the reaction be run in the presence of an aliphatic hydrocarbon such as pentane, hexane, heptane and the like or an ether such as diethylether or tetrahydrofuran, the latter being especially preferred. The temperature of the reaction is not critical, but it is preferred that the reaction be run at a temperature of from about −40° to 15° C., preferably from about −15° to +5° C. The reaction may be run from about 1 to 10 hours, preferably from about 1.5 to 2.5 hours. The product of the compound of formula (II) may be recovered using conventional techniques, e.g., filtration or it may be employed in situ as a starting material in the preparation of the compounds of formula (I).

Many of the compounds of formula (III) and (IV) are known and may be prepared by methods described in the literature. The compounds of formulae (III) and (IV) not specifically described may be prepared from known starting materials by analogous methods.

The compounds of formula (II) may also exist in the following tautomeric form, and this tautomeric form is also included within the scope of this invention:

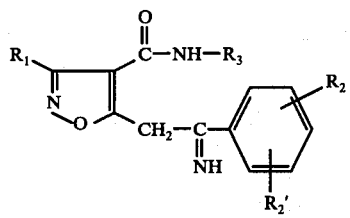

(IIa)

where $R_1$, $R_2$, $R_2'$ and $R_3$ are as defined above.

The compounds of formula (I) in which $R_1$ is lower alkyl, cycloalkyl, phenyl or substituted phenyl and $R_2$ is other

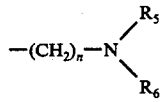

are useful as intermediates in the preparation of compounds having pharmaceutical activity as described in U.S. patent application Ser. Nos. 664,237 and 768,818 corresponding to German Offenlegungsschrift Nos. P-2633819.2 and P-2609127.0 respectively.

The compounds of formula (I) in which $R_1$ represents

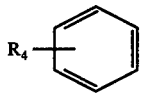

and $R_2'$ is hydrogen and $R_2$ is

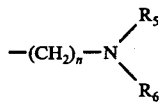

are useful as hypolipidemic agents as described in U.S. application Ser. No. 705,702.

EXAMPLE 1

5-(2-amino-2-phenylethenyl)-3-ethyl-N-methyl-isoxazole-4-carboxamide.

There is dissolved 72 grams (0.428 mole) of 3-ethyl-N,5-dimethyl-isoxazole-4-carboxamide in 1000 milliliters of dry tetrahydrofuran. The resulting mixture is then cooled to −5° C. While maintaining the temperature at −5° to 0° C., there is added over a period of 1 hour, a solution of 435 grams of 15% n-butyllithium in hexane, which is mixed for 1 hour at this temperature to form the lithium salt of 3-ethyl-N,5-dimethyl-4-isoxazole carboxamide. A solution of 50 grams (0.485 mole) of benzonitrile in 100 milliliters of dry tetrahydrofuran is then added to the lithium salt over a period of 1 hour. The resulting mixture is mixed for an additional hour while maintaining the temperature at −5° to 0° C., at which time there is added 100 milliliters of aqueous ammonium chloride. After 10 minutes of additional mixing, the water phase is then separated and the tetrahydrofuran solution is washed successively with 200 milliliters of water and 200 milliliters of saturated aqueous ammonium chloride. The tetrahydrofuran phase is then dried over sodium sulfate and concentrated to 300 milliliters. The concentrate is cooled to 0° C. and the title compound is precipitated by adding hexane to the concentrate, following which the solids are separated by filtration. The procedure is repeated with the mother liquor to obtain a total yield of 83 grams of 5-(2-amino-2-phenylethenyl)-3-ethyl-N-methyl-isoxazole-4-carboxamide; m.p. 125° to 132° C.; yield 71.5%. After further recrystallization from chloroform/hexane, the purified product has a m.p. of 137° to 139° C.

Following the above procedure and using in place of 3-ethyl-N,5-dimethyl-isoxazole-4-carboxamide an equivalent amount of (a) 3-cyclohexyl-N,5-dimethyl-isoxazole-4-carboxamide, there is obtained (a) 5-(2-amino-2-phenylethenyl)-3-cyclohexyl-N-methyl-isoxazole-4-carboxamide.

Again following the same procedure and using in place of benzonitrile an equivalent amount of (b) p-chlorobenzonitrile,
(c) p-fluorobenzonitrile,
(d) p-methylbenzonitrile,
(e) p-methoxybenzonitrile,
(f) m-fluorobenzonitrile,
(g) o-fluorobenzonitrile, or
(h) o-methylbenzonitrile, there is obtained (b) 5-(2-amino-2-[p-chlorophenyl]-ethenyl)-3-ethyl-N-methyl-isoxazole-4-carboxamide,
(c) 5-(2-amino-2-[p-fluorophenyl]-ethenyl)-3-ethyl-N-methyl-isoxazole-4-carboxamide,
(d) 5-(2-amino-2-[p-tolyl]-ethenyl)-3-ethyl-N-methyl-isoxazole-4-carboxamide,
(e) 5-(2-amino-2-[p-anisyl]-ethenyl)-3-ethyl-N-methyl-isoxazole-4-carboxamide,
(f) 5-(2-amino-2-[m-fluorophenyl]-ethenyl)-3-ethyl-N-methyl-isoxazole-4-carboxamide,
(g) 5-(2-amino-2-[o-fluorophenyl]-ethenyl)-3-ethyl-N-methyl-isoxazole-4-carboxamide, or
(h) 5-(2-amino-2-[o-tolyl]-ethenyl)-3-ethyl-N-methyl-isoxazole-4-carboxamide, respectively.

EXAMPLE 2

5-(2-amino-2-phenylethenyl)-N-methyl-3-phenyl-isoxazole-4-carboxamide.

A mixture of 100 grams (0.463 mole) of N,5-dimethyl-3-phenyl-isoxazole-4-carboxamide and 1000 milliliters of dry tetrahydrofuran is cooled to −5° C. While maintaining the temperature at −5° to 0° C., there is added over a period of 1 hour a solution of 435 grams (0.95 mole) of 15% n-butyllithium in hexane. The resulting mixture is stirred for 1 hour and while maintaining the temperature at −5° to 0° C. a solution of 50 grams (0.485 mole) of benzonitrile in 100 milliliters of dry tetrahydrofuran is added over a period of 1 hour. The resulting mixture is stirred for an additional hour at which time 100 milliliters of saturated ammonium chloride is added dropwise over a period of 15 to 20 minutes. The resulting solution is then mixed for 1 hour and 40 minutes and then diluted with 200 milliliters of water. The solids are then filtered off and washed three times with tetrahydrofuran/hexane. The solids are then dried under vacuum to give 94 grams of 5-(2-amino-2-phenylethenyl)-N-methyl-3-phenyl-isoxazole-4-carboxamide; m.p. 181° to 183° C. Further extraction from the mother liquors provide a total of 104 grams or 70.3% of the desired title compound. After further recrystallization from chloroform/methanol, the purified product has a melting point of 187° to 190° C.

Following the above procedure and using in place of N,5-dimethyl-3-phenyl-isoxazole-4-carboxamide, an equivalent amount of
(a) N,5-dimethyl-3-(p-chlorophenyl)-isoxazole-4-carboxamide,
(b) N,5-dimethyl-3-(p-fluorophenyl)-isoxazole-4-carboxamide,
(c) N,5-dimethyl-3-(p-tolyl)-isoxazole-4-carboxamide,
(d) N,5-dimethyl-3-(p-anisyl)-isoxazole-4-carboxamide,
(e) N,5-dimethyl-3-(m-trifluoromethylphenyl)-isoxazole-4-carboxamide,
there is obtained
(a) 5-(2-amino-2-phenylethenyl)-N-methyl-3-(p-chlorophenyl)-isoxazole-4-carboxamide,
(b) 5-(2-amino-2-phenylethenyl)-N-methyl-3-(p-fluorophenyl)-isoxazole-4-carboxamide,
(c) 5-(2-amino-2-phenylethenyl)-N-methyl-3-(p-tolyl)-isoxazole-4-carboxamide,
(d) 5-(2-amino-phenethenyl)-N-methyl-3-(p-anisyl)-isoxazole-4-carboxamide, or
(e) 5-(2-amino-2-phenylethenyl)-N-methyl-3-(m-trifluoromethylphenyl)-isoxazole-4-carboxamide, respectively.

Again following the same procedure and using in place of benzonitrile an equivalent amount of
(f) p-chlorobenzonitrile,
(g) p-fluorobenzonitrile,
(h) p-methylbenzonitrile,
(i) p-methoxybenzonitrile,
(j) m-trifluoromethylbenzonitrile,
(k) o-methylbenzonitrile, or
(l) 3,4-dichlorobenzonitrile
there is obtained
(f) 5-(2-amino-2-[p-chlorophenyl]-ethenyl)-3-phenyl-N-methyl-isoxazole-4-carboxamide,
(g) 5-(2-amino-2-[p-fluorophenyl]-ethenyl)-3-phenyl-N-methyl-isoxazole-4-carboxamide,
(h) 5-(2-amino-2-[p-tolyl]-ethenyl)-3-phenyl-N-methyl-isoxazole-4-carboxamide,
(i) 5-(2-amino-2-[p-anisyl]-ethenyl)-3-phenyl-N-methyl-isoxazole-4-carboxamide,
(j) 5-(2-amino-2-[m-trifluoromethylphenyl]-ethenyl)-3-phenyl-N-methyl-isoxazole-4-carboxamide,
(k) 5-(2-amino-2-[o-tolyl]-ethenyl)-3-phenyl-N-methyl-isoxazole-4-carboxamide, or
(l) 5-(2-amino-2-[3,4-dichlorophenyl]-ethenyl)-3-phenyl-N-methyl-isoxazole-4-carboxamide, respectively.

EXAMPLE 3

Following the procedures of Examples 1 and 2 and using in place of benzonitrile an equivalent amount of
(a) p-methylaminomethylbenzonitrile,
(b) p-dimethylaminomethylbenzonitrile,
(c) p-N-methyl-piperazinomethylbenzonitrile,
(d) p-piperidinomethylbenzonitrile, or
(e) p-morpholinomethylbenzonitrile,
there is obtained
(a) 5-(2-amino-2-[p-methylaminomethylphenyl]-ethenyl)-3-phenyl-N-methyl-isoxazole-4-carboxamide,
(b) 5-(2-amino-2-[p-dimethylaminomethylphenyl]-ethenyl)-3-phenyl-N-methyl-isoxazole-4-carboxamide,
(c) 5-(2-amino-2-[p-N-methyl-piperazinomethylphenyl]-ethenyl)-3-phenyl-N-methyl-isoxazole-4-carboxamide,
(d) 5-(2-amino-2-[p-piperidinomethylphenyl]-ethenyl)-3-phenyl-N-methyl-isoxazole-4-carboxamide, or
(e) 5-(2-amino-2-[p-morpholinomethylphenyl]-ethenyl)-3-phenyl-N-methyl-isoxazole-4-carboxamide, respectively.

EXAMPLE 4

5-methyl-3,6-diphenyl-isoxazolo[4,5-c]pyridine-4(5H)-one.

Under a nitrogen atmosphere, there is added 54 liters of acetone to 5.4 kilograms (16.9 mole) of 5-(2-amino-2-phenylethenyl)-N-methyl-3-phenyl-isoxazole-4-carboxamide at room temperature. To the resulting suspension, there is added 10.8 liters of approximately 5N hydrochloric acid while maintaining the temperature below 25° C. The mixture is then stirred overnight at 25° to 28° C. The resulting suspension is diluted with 16 liters of water at room temperature, and after mixing for 15 minutes, the solids are then filtered off and washed three times with a mixture of acetone/water (2:1). The resulting solids are then dried under reduced pressure at 45° C. to obtain 3.86 kilograms of 5-methyl-3,6-diphenyl-isoxazolo[4,5-c]pyridine-4(5H)-one; m.p. 145° to 148° C. The mother liquor is then concentrated under reduced pressure maintaining the temperature below 50° C. The mother liquor is then cooled to 20° C., the solids filtered off and washed three times with acetone/water (2:1) to obtain a second crop of 290 grams of 5-methyl-3,6-diphenyl-isoxazolo[4,5-c]pyridine-4(5H)-one; m.p. 140° to 145° C.; Yield 81%.

Following the above procedure and using in place of 5-(2-amino-2-phenylethenyl)-N-methyl-3-phenyl-isoxazole-4-carboxamide, an equivalent amount of
(a) 5-(2-amino-2-phenylethenyl)-3-ethyl-N-methyl-isoxazole-4-carboxamide,
(b) 5-(2-amino-2-phenylethenyl)-3-cyclohexyl-N-methyl-isoxazole-4-carboxamide,
(c) 5-(2-amino-2-[p-chlorophenyl]-ethenyl)-3-ethyl-N-methyl-isoxazole-4-carboxamide, (d) 5-(2-amino-2-[p-fluorophenyl]-ethenyl)-3-ethyl-N-methyl-isoxazole-4-carboxamide, (e) 5-(2-amino-2-[p-tolyl]-ethenyl)-3-ethyl-N-methyl-isoxazole-4-carboxamide, (f) 5-(2-amino-2-[p-anisyl]-ethenyl)-3-ethyl-N-methyl-isoxazole-4-carboxamide, (g) 5-(2-amino-2-[m-fluorophenyl]-ethenyl)-3-ethyl-N-methyl-isoxazole-4-carboxamide, (h) 5-(2-amino-2-[o-fluorophenyl]-ethenyl)-3-ethyl-N-methyl-isoxazole-4-carboxamide, (i) 5-(2-amino-2-[o-tolyl]-ethenyl)-3-ethyl-N-methyl-isoxazole-4-carboxamide, (j) 5-(2-amino-2-phenylethenyl)-N-methyl-3-(p-chlorophenyl)-isoxazole-4-carboxamide, (k) 5-(2-amino-2-phenylethenyl)-N-methyl-3-(p-fluorophenyl)-isoxazole-4-carboxamide, (l) 5-(2-amino-2-phenylethenyl)-N-methyl-3-(p-tolyl)-isoxazole-4-carboxamide, (m) 5-(2-amino-2-phenylethenyl)-N-methyl-3-(m-trifluoromethylphenyl)-isoxazole-4-carboxamide, (n) 5-(2-amino-2-[p-chlorophenyl]-ethenyl)-3-phenyl-N-methyl-isoxazole-4-carboxamide, (o) 5-(2-amino-2-[p-fluorophenyl]-ethenyl)-3-phenyl-N-methyl-isoxazole-4-carboxamide, (p) 5-(2-amino-2-[p-tolyl]-ethenyl)-3-phenyl-N-methyl-isoxazole-4-carboxamide, (q) 5-(2-amino-2-[p-anisyl]-ethenyl)-3-phenyl-N-methyl-isoxazole-4-carboxamide, (r) 5-(2-amino-2-[m-trifuoromethylphenyl]-ethenyl)-N-methyl-isoxazole-4-carboxamide, (s) 5-(2-amino-2-[o-tolyl]-ethenyl)-3-phenyl-N-methyl-isoxazole-4-carboxamide, (t) 5-(2-amino-2-[3,4-dichlorophenyl]-ethenyl)-3-phenyl-N-methyl-isoxazole-4-carboxamide, (u) 5-(2-amino-2-[p-methylaminomethylphenyl]-ethenyl)-3-phenyl-N-methyl-isoxazole-4-carboxamide, (v) 5-(2-amino-2-[p-dimethylaminomethylphenyl]-ethenyl)-3-phenyl-N-methyl-isoxazole-4-carboxamide, (w) 5-(2-amino-2-[p-N-methyl-piperazinomethylphenyl]-ethenyl)-3-phenyl-N-methyl-isoxazole-4-carboxamide, (x) 5-(2-amino-2-[p-piperidinomethylphenyl]-ethenyl)-3-phenyl-N-methyl-isoxazole-4-carboxamide, or (y) 5-(2-amino-2-[p-morpholinomethylphenyl]-ethenyl)-3-phenyl-N-methyl-isoxazole-4-carboxamide, there is obtained (a) 3-ethyl-5-methyl-6-phenyl-isoxazolo[4,5-c]pyridin-4(5H)-one, (b) 3-cyclohexyl-5-methyl-6-phenyl-isoxazolo[4,5-c]pyridin-4(5H)-one, (c) 3-ethyl-5-methyl-6-(p-chlorophenyl)-isoxazolo[4,5-c]pyridin-4(5H)-one, (d) 3-ethyl-5-methyl-6-(p-fluorophenyl)-isoxazolo[4,5-c]pyridin-4(5H)-one, (e) 3-ethyl-5-methyl-6-(p-tolyl)-isoxazolo[4,5-c]pyridin-4(5H)-one, (f) 3-ethyl-5-methyl-6-(p-anisyl)-isoxazolo[4,5-c]pyridin-4(5H)-one, (g) 3-ethyl-5-methyl-6-(m-fluorophenyl)-isoxazolo[4,5-c]pyridin-4(5H)-one, (h) 3-ethyl-5-methyl-6-(o-fluorophenyl)-isoxazolo[4,5-c]pyridin-4(5H)-one, (i) 3-ethyl-5-methyl-6-(o-tolyl)-isoxazolo[4,5-c]pyridin-4(5H)-one, (j) 5-methyl-3-(p-chlorophenyl)-6-phenyl-isoxazolo[4,5-c]pyridin-4(5H)-one, (k) 5-methyl-3-(p-fluorophenyl)-6-phenyl-isoxazolo[4,5-c]pyridin-4(5H)-one, (l) 5-methyl-3-(p-tolyl)-6-phenyl-isoxazolo[4,5-c]pyridin-4(5H)-one, (m) 5-methyl-3-(m-trifluoromethylphenyl)-6-phenyl-isoxazolo[4,5-c]pyridin-4(5H)-one, (n) 5-methyl-3-phenyl-6-(p-chlorophenyl)-isoxazolo[4,5-c]pyridin-4(5H)-one, (o) 5-methyl-3-phenyl-6-(p-fluorophenyl)-isoxazolo[4,5-c]pyridin-4(5H)-one, (p) 5-methyl-3-phenyl-6-(p-tolyl-isoxazolo[4,5-c]pyridin-4(5H)-one, (q) 5-methyl-3-phenyl-6-(p-anisyl-isoxazolo[4,5-c]pyridin-4(5H)-one, (r) 5-methyl-3-phenyl-6-(m-trifluoromethylphenyl)-isoxazolo[4,5-c]pyridin-4(5H)-one, (s) 5-methyl-3-phenyl-6-(o-tolyl)-isoxazolo[4,5-c]pyridin-4(5H)-one, (t) 5-methyl-3-phenyl-6-(3,4-dichlorophenyl)-isoxazolo[4,5-c]pyridin-4(5H)-one, (u) 5-methyl-3-phenyl-6-(p-[methylaminomethyl]phenyl)-isoxazolo[4,5-c]pyridin-4(5H)-one, (v) 5-methyl-3-phenyl-6-(p-dimethylaminomethyl]phenyl)-isoxazolo[4,5-c]pyridin-4(5H)-one, (w) 5-methyl-3-phenyl-6-(p-[N-methyl-piperazinomethyl]phenyl)-isoxazolo[4,5-c]pyridin-4(5H)-one, (x) 5-methyl-3-phenyl-6-(p-[piperidinomethyl]phenyl)-isoxazolo[4,5-c]pyridin-4(5H)-one, or (y) 5-methyl-3-phenyl-6-(p-[morpholinomethyl]phenyl)-isoxazolo[4,5-c]pyridin-4-one, respectively.

What is claimed is:

1. A process for preparing a compound of the formula

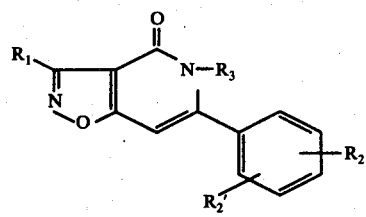

which comprises reacting a compound of the formula

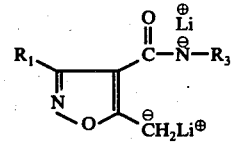

with a compound of the formula

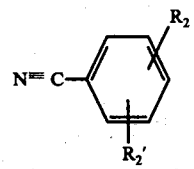

in the presence of an inert organic solvent to form an intermediate of the formula

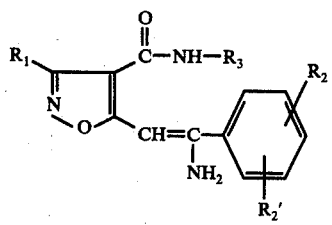

and thereafter cyclizing said intermediate under an inert atmosphere with an inorganic acid in the presence of a water-miscible solvent, wherein $R_1$ represents lower alkyl, cycloalkyl, or

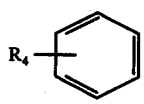

where $R_2$, $R_2'$ and $R_4$ each independently represent hydrogen, halo having an atomic weight of about 19 to 36, lower alkyl, lower alkoxy, or trifluoromethyl, and when $R_1$ represents

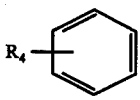

and $R_2'$ represents hydrogen, $R_2$ may also represent

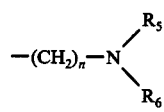

wherein $R_5$ and $R_6$ independently represent hydrogen or lower alkyl or together with N represent

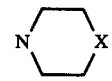

where
 X is $CH_2$, O or $N\text{-}CH_3$, and
 $n$ is 1 to 3, and
 $R_3$ represents lower alkyl.

2. The process according to claim 1 in which the inorganic acid is hydrochloric acid.

3. The process according to claim 1 in which the cyclization is carried out at a temperature of from about 15° to 100° C.

4. The process according to claim 1 in which the cyclization is carried out at a temperature of from about 25° to 30° C.

5. The process according to claim 1 in which the cyclization is carried out in the presence of acetone.

6. The process according to claim 1 in which the cyclization is carried out under a nitrogen atmosphere.

7. The process according to claim 1 wherein the reaction for preparing the intermediate is carried out at a temperature of from about −40° to 15° C.

8. The process according to claim 1 wherein the reaction for preparing the intermediate is carried out at a temperature of from about −15° to +5° C.

* * * * *